United States Patent
Libbus et al.

(10) Patent No.: US 8,401,672 B2
(45) Date of Patent: *Mar. 19, 2013

(54) METHOD AND APPARATUS FOR CONTROLLING AUTONOMIC BALANCE USING NEURAL STIMULATION

(75) Inventors: Imad Libbus, St. Paul, MN (US); Andrew P. Kramer, Marine on St. Croix, MN (US); Julio C. Spinelli, Lakewood Ranch, FL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/248,161

(22) Filed: Sep. 29, 2011

(65) Prior Publication Data
US 2012/0022608 A1 Jan. 26, 2012

Related U.S. Application Data

(60) Continuation of application No. 12/483,031, filed on Jun. 11, 2009, now Pat. No. 8,032,215, which is a division of application No. 11/124,791, filed on May 9, 2005, now Pat. No. 7,561,923.

(51) Int. Cl.
*A61N 1/05* (2006.01)
*A61N 1/18* (2006.01)

(52) U.S. Cl. .......................... 607/118; 607/149

(58) Field of Classification Search .............. 607/9, 45, 607/118; 600/528
See application file for complete search history.

(56) References Cited

U.S. PATENT DOCUMENTS

| | | | |
|---|---|---|---|
| 5,203,326 A | 4/1993 | Collins | |
| 5,700,282 A | 12/1997 | Zabara | |
| 6,006,134 A | 12/1999 | Hill et al. | |
| 6,210,344 B1 * | 4/2001 | Perin et al. | 600/528 |
| 6,292,698 B1 | 9/2001 | Duffin et al. | |
| 6,622,041 B2 | 9/2003 | Terry, Jr. et al. | |
| 6,678,547 B2 | 1/2004 | Carlson et al. | |
| 6,748,272 B2 | 6/2004 | Carlson et al. | |
| 6,879,859 B1 * | 4/2005 | Boveja | 607/45 |
| 7,069,070 B2 | 6/2006 | Carlson et al. | |
| 7,123,959 B2 * | 10/2006 | Cates | 607/9 |
| 7,277,761 B2 | 10/2007 | Shelchuk | |
| 7,561,923 B2 * | 7/2009 | Libbus et al. | 607/118 |
| 8,032,215 B2 | 10/2011 | Libbus et al. | |
| 2002/0099419 A1 | 7/2002 | Cohen et al. | |
| 2003/0045909 A1 * | 3/2003 | Gross et al. | 607/9 |
| 2003/0045914 A1 | 3/2003 | Cohen et al. | |
| 2003/0181951 A1 | 9/2003 | Cates | |
| 2004/0172094 A1 | 9/2004 | Cohen et al. | |

(Continued)

FOREIGN PATENT DOCUMENTS

| | | |
|---|---|---|
| EP | 0688577 A1 | 12/1995 |
| EP | 1486232 A2 | 12/2004 |

(Continued)

OTHER PUBLICATIONS

"U.S. Appl. No. 11/124,791 Notice of Allowance mailed Mar. 13, 2009", 4 pgs.

(Continued)

*Primary Examiner* — Carl H. Layno
*Assistant Examiner* — Jon-Eric C. Morales
(74) *Attorney, Agent, or Firm* — Schwegman Lundberg & Woessner, P.A.

(57) ABSTRACT

A neural stimulation system senses autonomic activities and applies neural stimulation to sympathetic and parasympathetic nerves to control autonomic balance. The neural stimulation system is capable of delivering neural stimulation pulses for sympathetic excitation, sympathetic inhibition, parasympathetic excitation, and parasympathetic inhibition.

20 Claims, 11 Drawing Sheets

U.S. PATENT DOCUMENTS

| | | |
|---|---|---|
| 2004/0199210 A1 | 10/2004 | Shelchuk |
| 2004/0243182 A1 | 12/2004 | Cohen et al. |
| 2005/0038490 A1 | 2/2005 | Gross et al. |
| 2005/0090719 A1 | 4/2005 | Scheiner et al. |
| 2005/0261741 A1 | 11/2005 | Libbus et al. |
| 2006/0106429 A1 | 5/2006 | Libbus et al. |
| 2006/0135998 A1 | 6/2006 | Libbus et al. |
| 2006/0161208 A1 | 7/2006 | Pastore et al. |
| 2006/0161209 A1 | 7/2006 | Pastore et al. |
| 2006/0206154 A1 | 9/2006 | Moffitt et al. |
| 2006/0253161 A1 | 11/2006 | Libbus et al. |
| 2009/0248119 A1 | 10/2009 | Libbus et al. |

FOREIGN PATENT DOCUMENTS

| | | |
|---|---|---|
| WO | WO-2006122148 A2 | 11/2006 |
| WO | WO-2006122148 A3 | 11/2006 |

OTHER PUBLICATIONS

"U.S. Appl. No. 11/124,791, Advisory Action mailed Nov. 27, 2007", 3 pgs.

"U.S. Appl. No. 11/124,791, Advisory Action mailed Dec. 10, 2008", 3 pgs.

"U.S. Appl. No. 11/124,791, Final Office Action mailed Sep. 13, 2007", 8 pgs.

"U.S. Appl. No. 11/124,791, Non-Final Office Action mailed Mar. 25, 2008", 10 pgs.

"U.S. Appl. No. 11/124,791, Response filed Nov. 13, 2007 to Final Office Action mailed Sep. 13, 2007", 11 pgs.

"U.S. Appl. No. 11/124,791, Response filed Nov. 17, 2008 to Final Office Action mailed Sep. 17, 2008", 12 pgs.

"U.S. Appl. No. 11/124,791, Response filed Jun. 24, 2008 to Non-Final Office Action mailed Mar. 25, 2008", 11 pgs.

"U.S. Appl. No. 11/124,791, Response filed Aug. 1, 2007 to Non-Final Office Action mailed May 3, 2007", 24 pgs.

"U.S. Appl. No. 11/124,791, Supplemental Response filed Feb. 17, 2009 to Final Office Action mailed Sep. 17, 2008 and Advisory Action mailed Dec. 10, 2008", 10 pgs.

"U.S. Appl. No. 11/124,791, Supplemental Response filed Dec. 13, 2007 to Final Office Action mailed Sep. 13, 2007 and Advisory Action mailed Nov. 27, 2007", 11 pgs.

"U.S. Appl. No. 12/483,031, Non Final Office Action mailed Dec. 28, 2010", 11 pgs.

"U.S. Appl. No. 12/483,031, Notice of Allowance mailed Jun. 1, 2011", 7 pgs.

"U.S. Appl. No. 12/483,031, Response filed Mar. 28, 2011 to Non Final Office Action mailed Dec. 28, 2010", 10 pgs.

"U.S. Appl. No. 11/124,791, Final Office Action mailed Sep. 17, 2008", 10 pgs.

"European Application Serial No. 06770144.1, Communication dated Oct. 2, 2009", 4 pgs.

"European Application Serial No. 06770144.1, Communication mailed May 6, 2009", 3 pgs.

"European Application Serial No. 06770144.1, Response filed Sep. 16, 2009 to Communication mailed May 6, 2009", 6 pgs.

"International Application Serial No. PCT/US2006/017971, International Search Report and Written Opinion mailed Oct. 20, 2006", 16 pgs.

Abraham, W T, "Cardiac Resynchronization in Chronic Heart Failure", New England Journal of Medicine, 346(24), (Jul. 13, 2002), 1845-1853.

Brockway, M., "Controlled Titration of Neurostimulation Therapy", U.S. Appl. No. 11/468,143, filed Aug. 29, 2006, 26 pgs.

Libbus, I., "Safety Control System for Implantable Neural Stimulator", U.S. Appl. No. 11/135,883, filed May 24, 2005, 43 pgs.

Nolan, J., et al., "Prospective Study of Heart Rate Variability and Mortality in Chronic Heart Failure: Results of the United Kingdom Heart Failure Evaluation and Assessment of Risk Trial (UK-Heart).", Circulation, 98(15), (1998), 1510-1516.

Sigurdsson, A., et al., "The Role of Neurohormonal Activation in Chronic Heart Failure and Postmyocardial Infarction", American Heart Journal, 132(1, Part 2), (Jul. 1996), 229-234.

Vanoli, E., et al., "Vagal Stimulation and Prevention of Sudden Death in Conscious Dogs With a Healed Myocardial Infarction", Circulation Research, 68(5), (May 1991), 1471-1481.

"European Application Serial No. 06770144.1, Response filed Feb. 12, 2010 to Office Action mailed Oct. 2, 2009", 8 pgs.

"Japanese Application Serial No. 2008-511286, Office Action mailed Nov. 14, 2011", (w/ English Translation), 7 pgs.

"Japanese Application Serial No. 2008-511286, Response filed Feb. 14, 2012 to Office Action mailed Nov. 14, 2011", (English Translation of Amended Claims), 4 pgs.

\* cited by examiner

METHOD AND APPARATUS FOR CONTROLLING AUTONOMIC BALANCE USING NEURAL STIMULATION

CLAIM OF PRIORITY

This application is a continuation of U.S. application Ser. No. 12/483,031, filed Jun. 11, 2009, now issued as U.S. Pat. No. 8,032,215, which is a divisional of U.S. application Ser. No. 11/124,791, filed May 9, 2005, now issued as U.S. Pat. No. 7,561,923, each of which are hereby incorporated by reference in its entirety.

TECHNICAL FIELD

This document generally relates to medical devices and particularly to a neural stimulation system that controls autonomic balance.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are accomplished by cyclic contractions of the myocardium (heart muscles). In a normal heart, the sinoatrial node generates electrical impulses called action potentials. The electrical impulses propagate through an electrical conduction system to various regions of the heart to excite the myocardial tissue of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction system and/or deteriorated myocardial tissue result in an impaired hemodynamic performance, including a diminished blood supply to the heart and the rest of the body.

The hemodynamic performance is modulated by neural signals in portions of the autonomic nervous system. For example, the myocardium is innervated with sympathetic and parasympathetic nerves. Neural activities on these nerves are known to regulate, among other things, heart rate, blood pressure, and myocardial contractility. Autonomic dysfunction is associated with cardiac dysfunctions and poor hemodynamic performance. For example, in heart failure patients, reduced autonomic balance (increase in sympathetic tone and decrease in parasympathetic tone) is known to be associated with left ventricular dysfunction and increased mortality. Examples of other conditions of autonomic dysfunction, collectively termed as dysautonomia, include postural orthostatic tachycardia syndrome (POTS), neurocardiogenic syncope (NCS), pure autonomic failure (PAF), and multiple system atrophy (MSA). Patients having autonomic dysfunction and the associated cardiac dysfunctions can potentially benefit from controlling the autonomic balance. For example, increasing parasympathetic tone and decreasing sympathetic tone may protect the myocardium by controlling adverse remodeling and preventing arrhythmias after myocardial infarction. Patients with bradycardia-tachycardia syndrome, a variant of sick sinus syndrome characterized by alternating periods of slow and rapid heart rate, may also benefit from regulation of autonomic function. For these and other reasons, there is a need for a means to treat autonomic dysfunction or cardiac dysfunction by controlling autonomic balance.

SUMMARY

A neural stimulation system senses autonomic activities and applies neural stimulation to sympathetic and parasympathetic nerves to control autonomic balance. The neural stimulation system is capable of delivering neural stimulation pulses for sympathetic excitation, sympathetic inhibition, parasympathetic excitation, and parasympathetic inhibition.

In one embodiment, a neural stimulation system includes a stimulation output circuit, an autonomic balance monitoring circuit, and a stimulation control circuit. The stimulation output circuit delivers sympathetic stimulation pulses and parasympathetic stimulation pulses. The autonomic balance monitoring circuit senses one or more signals indicative of autonomic activities. The stimulation control circuit includes a sympathetic stimulation controller and a parasympathetic stimulation controller. The sympathetic stimulation controller controls the delivery of the sympathetic stimulation pulses for sympathetic excitation and sympathetic inhibition. The parasympathetic stimulation controller controls the delivery of the parasympathetic stimulation pulses for parasympathetic excitation and parasympathetic inhibition.

In one embodiment, a method for neural stimulation provides for sympathetic excitation, sympathetic inhibition, parasympathetic excitation, and/or parasympathetic inhibition. One or more signals indicative of autonomic activities are sensed. Delivery of sympathetic and parasympathetic stimulation pulses is controlled using feedback control, with one or more inputs including the one or more signals indicative of autonomic activities. This includes controlling the delivery of the sympathetic stimulation pulses for sympathetic excitation and sympathetic inhibition and controlling the delivery of the parasympathetic stimulation pulses for parasympathetic excitation and parasympathetic inhibition.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

Figure 1:
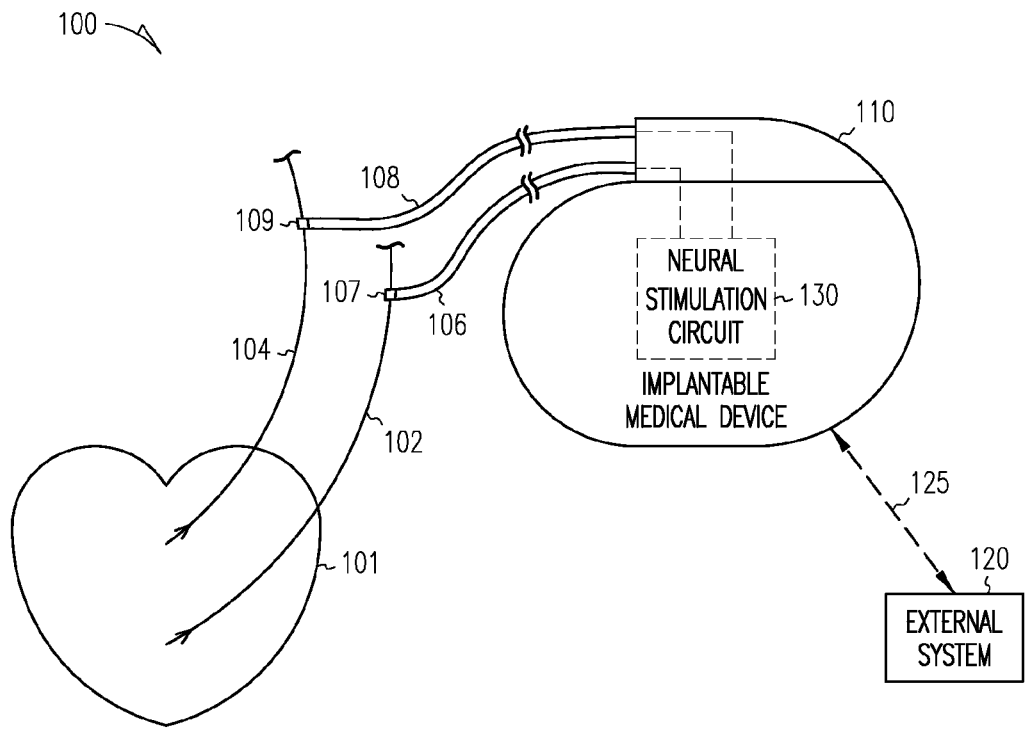
FIG. 1 is an illustration of an embodiment of a neural stimulation system for controlling autonomic balance and portions of an environment in which the neural stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a neural stimulation system that senses and controls autonomic balance. Implantable neural leads include electrodes for placement in or about sympathetic and parasympathetic nerves to sense neural activities from and deliver neural stimulation pulses to these nerves. The neural stimulation pulses include electrical pulses that stimulate one or more nerves. An implantable neural stimulation device delivers the neural stimulation pulses to the sympathetic and parasympathetic nerves to control autonomic balance by using a selective combination of sympathetic excitation (excitatory stimulation of the sympathetic nervous system), sympathetic inhibition (inhibitory stimulation of the sympathetic nervous system), parasympathetic excitation (excitatory stimulation of the parasympathetic nervous system), and parasympathetic inhibition (inhibitory stimulation of the parasympathetic nervous system). Such a device is capable of delivering a therapy with a broad range of therapeutic effects and/or overall stimulation intensity. For example, delivering the sympathetic inhibition and the parasympathetic excitation simultaneously has the potential of providing for a substantially stronger effect and/or additional therapeutic effects when compared to delivering either the sympathetic inhibition or the parasympathetic excitation alone. Simultaneous delivery of excitatory and inhibitory stimulation to one of the sympathetic and parasympathetic nervous system provides for a broader range of control of systemic as well as localized physiological functions. For example, delivering excitatory and inhibitory stimulation simultaneously to two efferent nerves of the sympathetic or parasympathetic nervous system may allow individualized control of two organs or two portions of an organ each innervated by one of these efferent nerves. Simultaneous delivery of excitatory stimulation to an afferent nerve and inhibitory stimulation to an efferent nerve, or inhibitory stimulation to an afferent nerve and excitatory stimulation to an efferent nerve, of the same nervous system allows simultaneous general control of systemic activities (e.g., central nervous system activities) and specific control of local activities (e.g., peripheral organ activities).

FIG. 1 is an illustration of an embodiment of a neural stimulation system 100 for controlling autonomic balance and portions of an environment in which system 100 is used. System 100 includes implantable medical device 110 that delivers neural stimulation pulses through leads 106 and 108, an external system 120, and a telemetry link 125 providing for communication between implantable medical device 110 and external system 120.

System 100 controls autonomic balance by delivering neural stimulation pulses to sympathetic and parasympathetic nerves. For illustrative purpose only, FIG. 1 shows that lead 106 includes an electrode 107 coupled to a nerve 102 of the sympathetic nervous system, and lead 108 includes an electrode 109 coupled to a nerve 104 of the parasympathetic nervous system. Nerves 102 and 104 innervate a heart 101. In various embodiments, implantable medical device 110 provides neural stimulation to any one or more nerves through one or more implantable neural leads to control autonomic balance. Such implantable neural leads each include at least one electrode for sensing neural activities and delivering neural stimulation pulses. Examples of such implantable neural leads include an expandable stimulation lead having an electrode for placement in a pulmonary artery in a proximity of a high concentration of baroreceptors, a transvascular lead having an electrode for placement proximal to a cardiac fat pad, an epicardial lead having an electrode for placement in a cardiac fat pad, a lead having a cuff electrode for placement around an aortic, carotid, or vagus nerve, an intravascularly fed lead having an electrode for placement proximal to the aortic, carotid, or vagus nerve for transvascularly delivering the neural stimulation pulses to that nerve, and a lead having an electrode for placement in a spinal cord, on the spinal cord dorsal or ventral nerves, or in the sympathetic ganglia or nerves.

Implantable medical device 110 includes a neural stimulation circuit 130. Neural stimulation circuit 130 delivers sympathetic stimulation pulses (electrical pulses that stimulate one or more sympathetic nerves) and parasympathetic stimulation pulses (electrical pulses that stimulate one or more parasympathetic nerves). The delivery of the sympathetic stimulation pulses and the delivery of the parasympathetic stimulation pulses are individually controllable and coordinated. By controlling stimulation parameters, the sympathetic stimulation pulses are delivered to increase or decrease the sympathetic tone, and the parasympathetic stimulation pulses are delivered to increase or decrease the parasympathetic tone. In various embodiments, implantable medical device 110 is capable of sensing physiological signals and/or delivering therapies in addition to the neural stimulation. Examples of such additional therapies include cardiac pacing therapy, cardioversion/defibrillation therapy, cardiac resynchronization therapy (CRT), cardiac remodeling control therapy (RCT), drug therapy, cell therapy, and gene therapy. In various embodiments, implantable medical device 110 delivers the neural stimulation in coordination with one or more such additional therapies.

External system 120 communicates with implantable medical device 110 and provides for access to implantable medical device 110 by a physician or other caregiver. In one embodiment, external system 120 includes a programmer. In another embodiment, external system 120 is a patient management system including an external device communicating with implantable medical device 110 via telemetry link 125, a remote device in a relatively distant location, and a telecommunication network linking the external device and the remote device. The patient management system allows access to implantable medical device 110 from a remote location, for purposes such as monitoring patient status and adjusting therapies. In one embodiment, telemetry link 125 is an inductive telemetry link. In an alternative embodiment, telemetry link 125 is a far-field radio-frequency (RF) telemetry link. Telemetry link 125 provides for data transmission from implantable medical device 110 to external system 120. This includes, for example, transmitting real-time physiological data acquired by implantable medical device 110, extracting physiological data acquired by and stored in implantable medical device 110, extracting patient history data such as occurrences of arrhythmias and therapy deliveries recorded in implantable medical device 110, and/or extracting data indicating an operational status of implantable medical device 110 (e.g., battery status and lead impedance). Telemetry link 125 also provides for data transmission from external system 120 to implantable medical device 110. This includes, for example, programming implantable medical device 110 to acquire physiological data, programming implantable medical device 110 to perform at least one self-diagnostic test (such as for a device operational status), and/or programming implantable medical device 110 to deliver one or more therapies and/or to adjust the delivery of one or more therapies.

Figure 2:
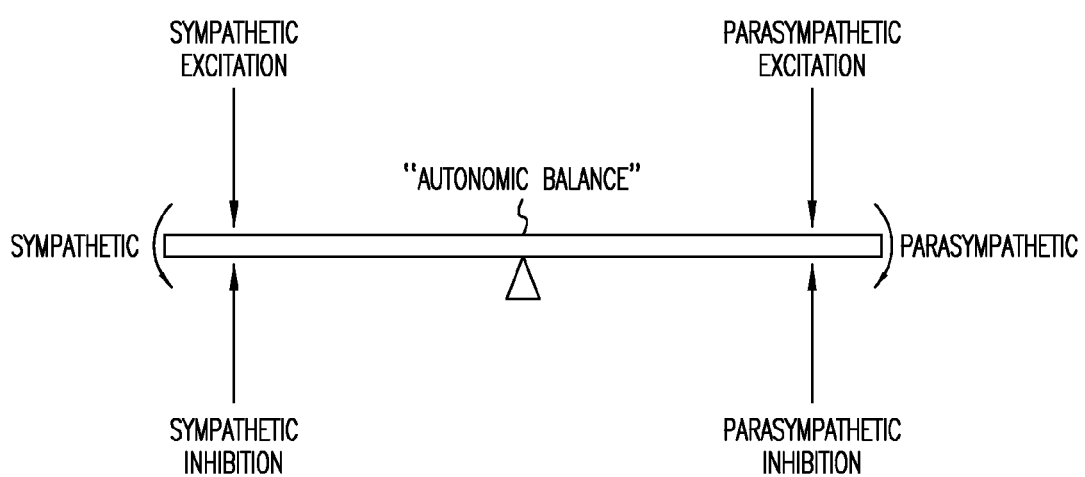
FIG. 2 is an illustration of an embodiment of a method for controlling autonomic balance by neural stimulation.

FIG. 2 is an illustration of an embodiment of a method for controlling autonomic balance by neural stimulation. A balance beam represents autonomic balance, which is shown in FIG. 2 as being in a balanced position. A counterclockwise rotation of the balance beam indicates that the autonomic balance shifts to the sympathetic nervous system, with a relative high sympathetic tone and a relatively low parasympathetic tone. A clockwise rotation of the balance beam indicates that the autonomic balance shifts to the parasympathetic nervous system, with a relative low sympathetic tone and a relatively high parasympathetic tone. As illustrated in FIG. 2, the balance of the beam, i.e., the autonomic balance, is controlled by applying one or more of sympathetic excitation, sympathetic inhibition, parasympathetic excitation, and parasympathetic inhibition. By controlling stimulation parameters, the sympathetic stimulation pulses are delivered for either sympathetic excitation, which increases the sympathetic tone, or sympathetic inhibition, which decreases the sympathetic tone. The parasympathetic stimulation pulses are delivered for either parasympathetic excitation, which increases the parasympathetic tone, or parasympathetic inhibition, which decreases the parasympathetic tone. A combination of the sympathetic excitation, sympathetic inhibition, parasympathetic excitation, and parasympathetic inhibition brings the balance beam to the balanced position or a desirable shifted position.

Figure 3:
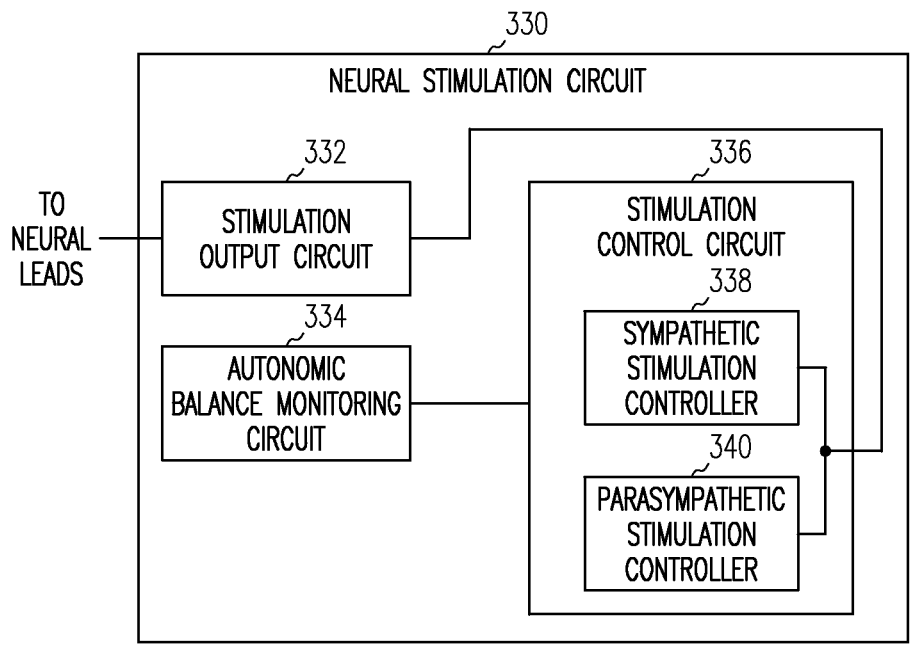
FIG. 3 is a block diagram illustrating an embodiment of a neural stimulation circuit of the neural stimulation system.

FIG. 3 is a block diagram illustrating an embodiment of a neural stimulation circuit 330, which is a specific embodiment of neural stimulation circuit 130. Neural stimulation circuit 330 includes a stimulation output circuit 332, an autonomic balance monitoring circuit 334, and a stimulation control circuit 336. Stimulation output circuit 332 delivers sympathetic stimulation pulses and parasympathetic stimulation pulses through one or more neural leads such as those discussed in this document. Autonomic balance monitoring circuit 334 senses one or more signals indicative of autonomic activities such as nerve traffic in one or more nerves of the autonomic nervous system or physiological activities affected by the autonomic activities. In various embodiments, the one or more signals indicative of autonomic activities include one or more signals indicative of the autonomic state. Stimulation control circuit 336 controls the delivery of neural stimulation pulses based on the one or more signals indicative of autonomic activities. Stimulation control circuit 336 includes a sympathetic stimulation controller 338 and a parasympathetic stimulation controller 340. Sympathetic stimulation controller 338 controls the delivery of the sympathetic stimulation pulses for the sympathetic excitation and the sympathetic inhibition. Parasympathetic stimulation controller 340 controls the delivery of the parasympathetic stimulation pulses for the parasympathetic excitation and the parasympathetic inhibition. Sympathetic stimulation controller 338 and parasympathetic stimulation controller 340 allow the delivery of the sympathetic stimulation pulses and the delivery of the parasympathetic stimulation pulses to be individually controllable. In one embodiment, stimulation output circuit 332, autonomic balance monitoring circuit 334, and stimulation control circuit 336 are housed in a hermetically sealed implantable housing to form an implantable medical device.

Figure 4:
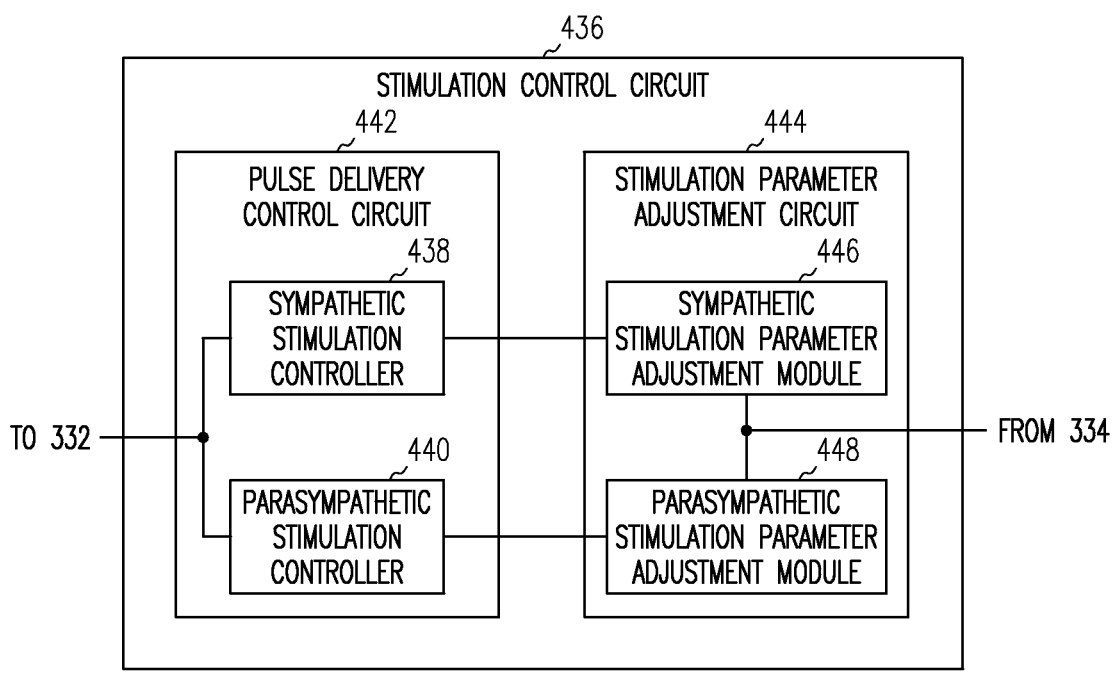
FIG. 4 is a block diagram illustrating an embodiment of a stimulation control circuit of the neural stimulation circuit.

FIG. 4 is a block diagram illustrating an embodiment of a stimulation control circuit 436, which is a specific embodiment of stimulation control circuit 336. Stimulation control circuit 436 controls the delivery of the sympathetic stimulation pulses and parasympathetic stimulation pulses based on the one or more signals indicative of autonomic activities sensed by autonomic balance monitoring circuit 334 and the programmed goals of autonomic balance monitoring circuit 334. Stimulation control circuit 436 includes a pulse delivery control circuit 442 and a stimulation parameter adjustment circuit 444.

Pulse delivery control circuit 442 controls the delivery of the sympathetic stimulation pulses and the parasympathetic stimulation pulses using a plurality of stimulation parameters received from stimulation parameter adjustment circuit 444. Pulse delivery control circuit 442 includes a sympathetic stimulation controller 438 and a parasympathetic stimulation controller 440. Sympathetic stimulation controller 438 controls the delivery of the sympathetic stimulation pulses for the sympathetic excitation and the sympathetic inhibition. Parasympathetic stimulation controller 440 controls the delivery of the parasympathetic stimulation pulses for parasympathetic excitation and parasympathetic inhibition. In one embodiment, the stimulation frequency determines whether the electrical stimulation pulses delivered to a nerve results in the excitation or inhibition of that nerve. The stimulation frequency is controlled by a stimulation parameter specifying the frequency at which the electrical stimulation pulses are delivered (in number of pulses per second, for example).

Alternatively, the stimulation frequency is controlled by a stimulation parameter specifying the interval between two consecutive electrical stimulation pulses (in milliseconds, for example). When the stimulation frequency is below a certain level, the electrical stimulation pulses delivered to a nerve excites that nerve, resulting in increased nerve traffic. When the stimulation frequency is above another certain level, the electrical stimulation pulses delivered to a nerve inhibits that nerve, resulting in decreased nerve traffic. In another embodiment, the stimulation polarity determines whether the electrical stimulation pulses delivered to a nerve results in the excitation or inhibition of that nerve. Axon action potentials are excited by a current depolarizing an axon and blocked by a current hyperpolarizing the axon. Thus, stimulation with cathodal current excites a nerve by exciting axon action potentials, and stimulation with anodal current inhibits the nerve by blocking axon action potentials. In a specific embodiment, the stimulation polarity is controlled by using bipolar electrode configuration on a nerve and controlling the direction of stimulation current flow between two electrodes. In a further embodiment, the stimulation polarity and intensity determine the direction of nerve traffic as a result of neural stimulation. When electrical stimulation pulses are delivered to a nerve using two electrodes in a bipolar configuration, the evoked axon action potentials propagate in both afferent and efferent directions of the axon when the stimulation intensity is within a certain range. When the stimulation intensity is above a certain level, "anodal block" occurs. The action potential is blocked in the direction from the cathode to the anode while stilling propagating in the direction from the anode to the cathode. This allows, for example, selection of excitatory stimulation or inhibitory stimulation of a nerve innervating an organ by controlling the stimulation polarity and intensity. The excitatory (efferent) stimulation is selected by designating the electrode closer to the central nervous system as the anode and setting the stimulation intensity to a level at which the anodal block occurs. The inhibitory (afferent) stimulation is selected by designating the electrode closer to the organ as the anode and setting the stimulation intensity to a level at which the anodal block occurs. The stimulation has the inhibitory effect because of the negative feedback reflex circuits.

Stimulation parameter adjustment circuit 444 adjusts the plurality of stimulation parameters used by pulse delivery control circuit 442 based on the one or more signals indicative of autonomic activities and the therapeutic objectives. The therapeutic objectives are programmed by mapping the autonomic state (input) to the stimulation parameters (output) using feedback control to shift the sensed autonomic state to a desired autonomic state. In one embodiment, stimulation parameter adjustment circuit 444 adjusts the plurality of stimulation parameters dynamically using feedback control with one or more inputs including the one or more signals indicative of autonomic activities. Examples of such signals indicative of autonomic activities include neural signals, surrogate signals, and physiological function signals. In one embodiment, stimulation parameter adjustment circuit 444 adjusts the plurality of stimulation parameters based on one or more neural signals. Neural activities indicated by the one or more neural signals provide for a direct measure of the autonomic state. In another embodiment, stimulation parameter adjustment circuit 444 adjusts the plurality of stimulation parameters based on one or more surrogate signals. A surrogate signal is a signal sensed as a measure or indication of the autonomic balance. In another embodiment, stimulation parameter adjustment circuit 444 adjusts the plurality of stimulation parameters based on one or more physiological function signals. Such physiological function signals are each a measure or an indication of effects of the autonomic balance. In various other embodiments, stimulation parameter adjustment circuit 444 adjusts the plurality of stimulation parameters based on a combination of two or more of the neural signal(s), the surrogate signal(s), and the physiological function signal(s). This allows adjustment of the stimulation parameters based on both the autonomic activities and their effects in selected physiological functions. In one embodiment, stimulation parameter adjustment circuit 444 adjusts the plurality of stimulation parameters based on the one or more neural signals and the one or more physiological function signals. In another embodiment, stimulation parameter adjustment circuit 444 adjusts the plurality of stimulation parameters based on the one or more surrogate signals and the one or more physiological function signals. The neural, surrogate, and physiological signals and their sensing are further discussed below, with reference to FIGS. 5-8.

In one embodiment, the plurality of stimulation parameters includes one or more sympathetic stimulation parameters and one or more parasympathetic stimulation parameters. The one or more sympathetic stimulation parameters control the delivery of the sympathetic stimulation pulses for the sympathetic excitation and the sympathetic inhibition. The one or more parasympathetic stimulation parameters control the delivery of the parasympathetic stimulation pulses for the parasympathetic excitation and the parasympathetic inhibition. In this embodiment, as illustrated in FIG. 4, stimulation parameter adjustment circuit 444 includes a sympathetic stimulation parameter adjustment module 446 and a parasympathetic stimulation parameter adjustment module 448. Sympathetic stimulation parameter adjustment module 446 adjusts the one or more sympathetic stimulation parameters. Parasympathetic stimulation parameter adjustment module 448 adjusts the one or more parasympathetic stimulation parameters.

In one embodiment, stimulation parameter adjustment circuit 444 adjusts the plurality of stimulation parameters based on a predetermined time schedule, in addition to the one or more signals indicative of autonomic activities. For example, a heart failure patient suffers from poor hemodynamic performance and adverse myocardial remodeling. To improve the hemodynamic performance, the autonomic balance is shifted to increase the sympathetic tone and/or decrease the parasympathetic tone. To control the myocardial remodeling, the autonomic balance is shifted to decrease the sympathetic tone and/or increase the parasympathetic tone. One example of a treatment strategy is to adjust the stimulation parameters based on a time schedule made according to the patient's anticipated daily activities. For example, the stimulation parameters are adjusted for increasing the sympathetic tone and/or decreasing the parasympathetic tone during the day and for decreasing the sympathetic tone and/or increasing the parasympathetic tone at night. In another embodiment, stimulation parameter adjustment circuit 444 adjusts the plurality of stimulation parameters based on a signal indicative of a need to shift the autonomic balance, in addition to the one or more signals indicative of autonomic activities. For example, for the same heart failure patient, an activity level signal is used to indicate the patient's gross physical activity level, which in turn indicates a need to increase hemodynamic performance. The activity level signal is sensed using an activity sensor such as an implantable accelerometer or piezoelectric crystal. When the activity level signal exceeds a predetermined threshold, the stimulation parameters are adjusted for increasing the sympathetic tone and/or decreasing the parasympathetic tone. This improves the patient's hemodynamic performance to meet the metabolic demand for the patient's activity, but may have undesirable effects in the myocardial remodeling. When the activity level signal falls below another predetermined threshold, the stimulation parameters are adjusted for decreasing the sympathetic tone and/or increasing the parasympathetic tone. This provides control of the myocardial remodeling when the metabolic demand is low. In another example, a patient suffering from brady-tachy syndrome has a cardiac rhythm oscillating between bradycardia and tachycardia. To treat the patient by regulating the heart rate, the autonomic balance is shifted when the heart rate falls into a bradycardia rate window or a tachycardia rate window. When the heart rate falls below a predetermined threshold, the stimulation parameters are adjusted for increasing the sympathetic tone and/or decreasing the parasympathetic tone, thereby increasing the patient's heart rate. When the heart rate exceeds a predetermined threshold, the stimulation parameters are adjusted for decreasing the sympathetic tone and/or increasing the parasympathetic tone, thereby decreasing the patient's heart rate.

In one embodiment, stimulation parameter adjustment circuit 444 is programmable via telemetry to adjust the plurality of stimulation parameters used by pulse delivery control circuit 442 according to therapeutic objectives set by a physician or other caregiver. The mapping between the one or more signals indicative of autonomic activities and the stimulation parameters is programmable with programmable parameters specifying the responsiveness of the feedback control. Such parameters affect, for example, how quickly the stimulation parameters are adjusted in response to a sensed change in the autonomic state, the sensitivity of the feedback control, the limits within which the autonomic state is to be adjusted or maintained, and the limits of the output level (e.g., stimulation intensity).

Figure 5:
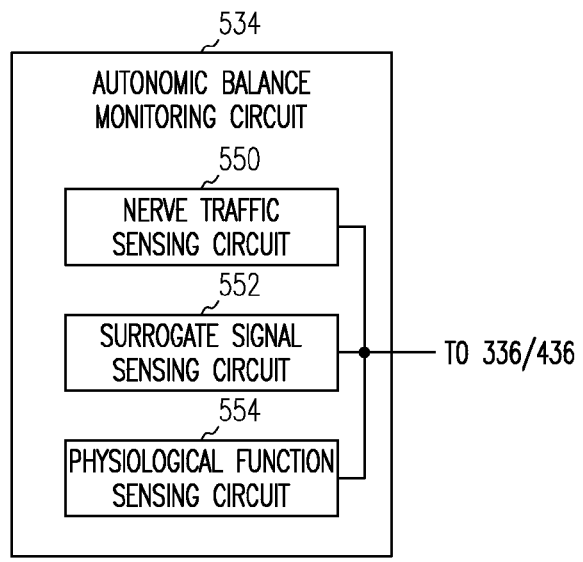
FIG. 5 is a block diagram illustrating an embodiment of an autonomic balance monitoring circuit of the neural stimulation circuit.

FIG. 5 is a block diagram illustrating an embodiment of an autonomic balance monitoring circuit 534, which is a specific embodiment of autonomic balance monitoring circuit 334. Autonomic balance monitoring circuit 534 provides stimulation control circuit 336 (or 436) with the one or more signals indicative of autonomic activities.

In one embodiment, as illustrated in FIG. 5, autonomic balance monitoring circuit 534 includes a nerve traffic sensing circuit 550, a surrogate signal sensing circuit 552, and a physiological function sensing circuit 554. In various embodiments, depending on which of the one or more signals indicative of autonomic activities are used by stimulation control circuit 336 (or 436), autonomic balance monitoring circuit 534 includes any one, a combination of any two, or a combination of all three of nerve traffic sensing circuit 550, surrogate signal sensing circuit 552, and physiological function sensing circuit 554.

Figure 6:
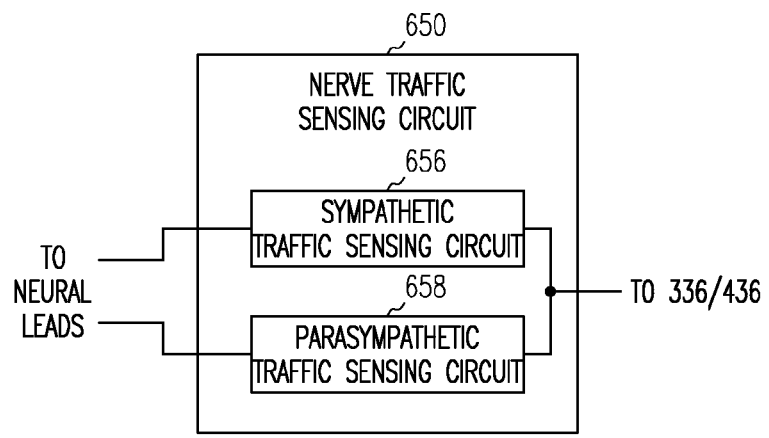
FIG. 6 is a block diagram illustrating an embodiment of a nerve traffic sensing circuit of the autonomic balance monitoring circuit.

FIG. 6 is a block diagram illustrating an embodiment of a nerve traffic sensing circuit 650, which is a specific embodiment of nerve traffic sensing circuit 550. Nerve traffic sensing circuit 650 senses one or more neural signals that directly indicate the autonomic state. Nerve traffic sensing circuit 650 includes a sympathetic traffic sensing circuit 656 and a parasympathetic traffic sensing circuit 658. Sympathetic traffic sensing circuit 656 sense at least one sympathetic neural signal indicative of sympathetic nerve traffic. Parasympathetic traffic sensing circuit 658 senses at least one parasympathetic neural signal indicative of parasympathetic nerve traffic.

Figure 7:
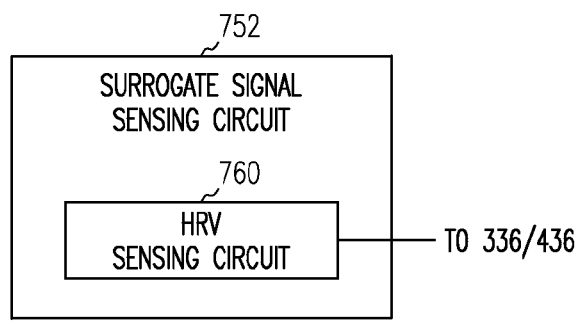
FIG. 7 is a block diagram illustrating an embodiment of a surrogate signal sensing circuit of the autonomic balance monitoring circuit.

FIG. 7 is a block diagram illustrating an embodiment of a surrogate signal sensing circuit 752, which is a specific embodiment of surrogate signal sensing circuit 552. Surrogate signal sensing circuit 752 senses one or more surrogate signals each indicative of autonomic activities and used as a measure of the autonomic state. Surrogate signal sensing circuit 752 includes a heart rate variability (HRV) sensing circuit 760 to sense HRV and produce an HRV signal. HRV is the beat-to-beat variance in cardiac cycle length over a period of time. The HRV signal is a signal representative of an HRV parameter that includes any parameter being a measure of the HRV, including any qualitative expression of the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. The LF/HF ratio is used to track trends in shifts of autonomic balance. For example, a substantial change in the LF/HF ratio indicates a change in systemic stress that indicates the degree to which the sympathetic nervous system is over-stimulated.

Figure 8:
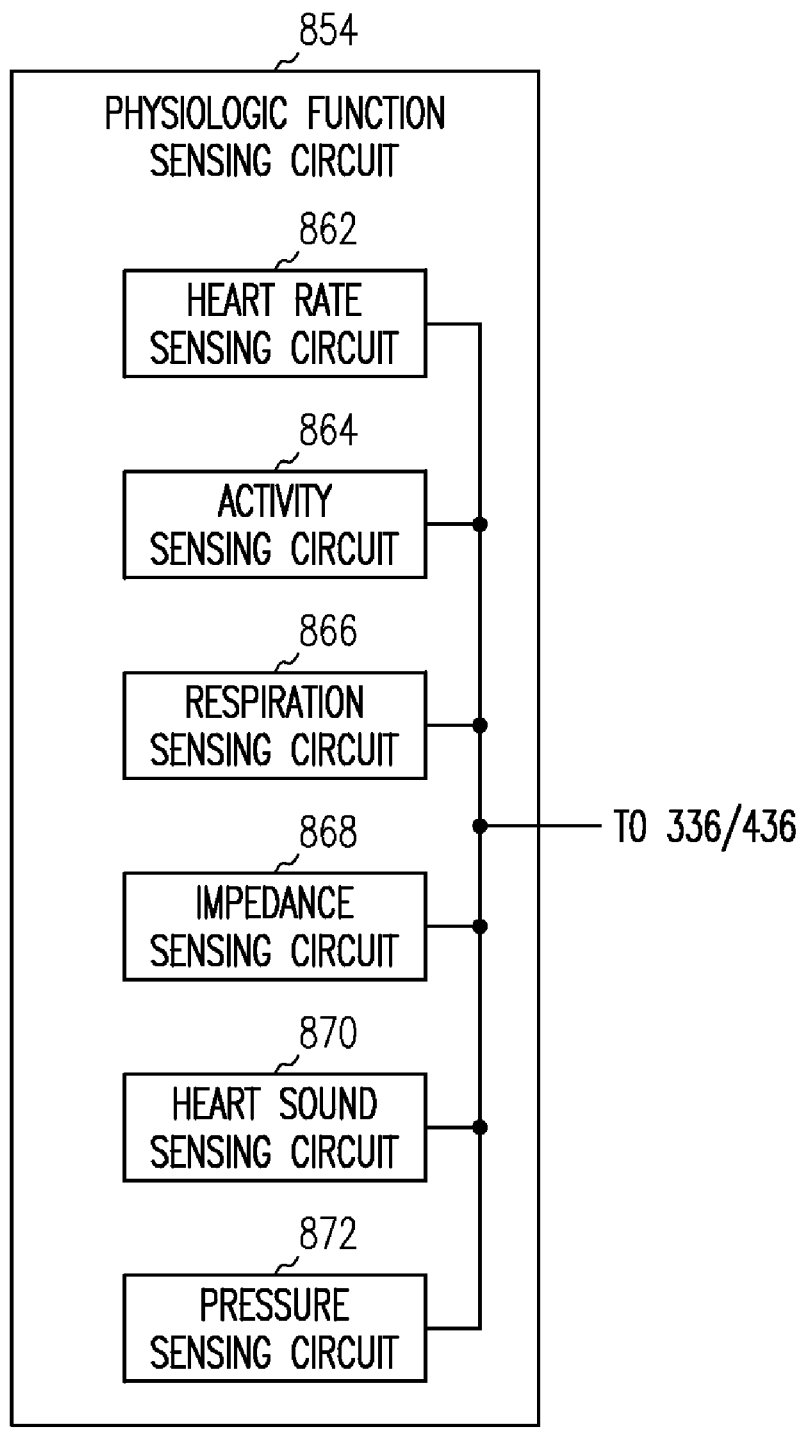
FIG. 8 is a block diagram illustrating an embodiment of a physiological function sensing circuit of the autonomic balance monitoring circuit.

FIG. 8 is a block diagram illustrating an embodiment of a physiological function sensing circuit 854, which is a specific embodiment of physiological function sensing circuit 554. Physiological function sensing circuit 854 senses one or more physiological function signals each affected by autonomic activities. Such a physiological function signal indicates a need to control the autonomic balance to result in a desirable change or restoration of a physiological function. Physiological function sensing circuit 854 includes one or more of a heart rate sensing circuit 862 to sense a heart rate and rhythm, an activity sensing circuit 864 to sense a physical activity level, a respiration sensing circuit 866 to sense a respiratory signal indicative of respiratory rate, rhythm tidal volume, and cardiac stroke volume, an impedance sensing circuit 868 to sense a signal indicative of stroke volume, such as a cardiac impedance or a transthoracic impedance, a heart sound sensing circuit 870 to sense a signal indicative of cardiac systolic and diastolic timing, ventricular contractility, and filling pressure, and a pressure sensing circuit 872 to sense a signal indicative of a blood pressure.

Figure 9:
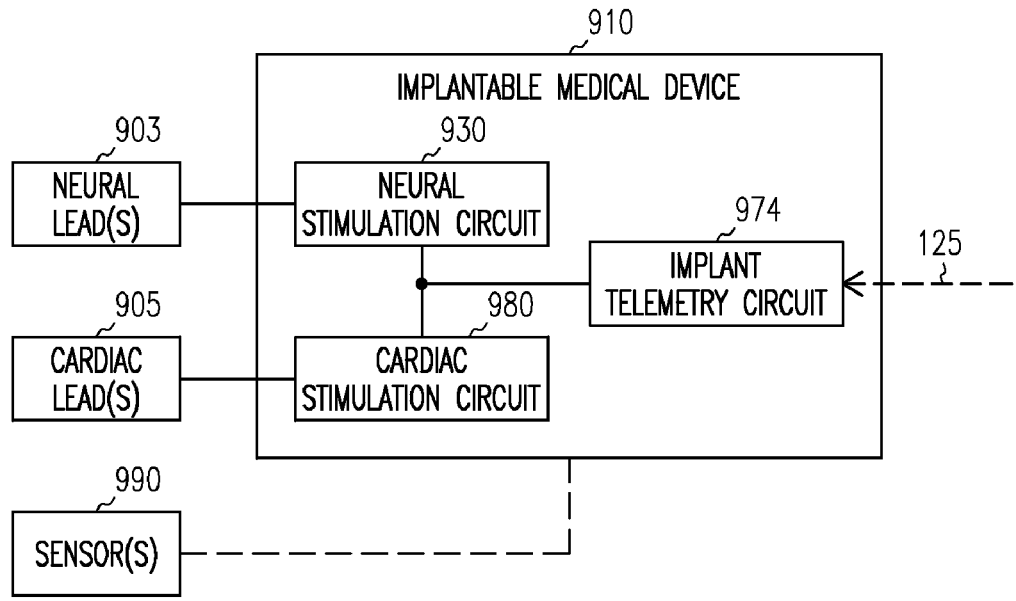
FIG. 9 is a block diagram illustrating an embodiment of an implantable medical device including the neural stimulation circuit and a cardiac stimulation circuit.

FIG. 9 is a block diagram illustrating an embodiment of an implantable medical device 910 coupled to neural lead(s) 903 and cardiac lead(s) 905. Implantable medical device 910, which is a specific embodiment of implantable medical device 110, is an integrated cardiac and neural stimulation device and includes a neural stimulation circuit 930, a cardiac stimulation circuit 980, and an implant telemetry circuit 974. Neural lead(s) 903 includes one or more implantable neural leads each including at least one electrode configured for sensing neural activities and delivering neural stimulation pulses. Cardiac lead(s) 905 includes one or more implantable cardiac stimulation leads each including at least one endocardial or epicardial electrode configured for sensing cardiac activities and delivering cardiac stimulation pulses. Neural stimulation circuit 930 is a specific embodiment of neural stimulation circuit 130 that communicates with cardiac stimulation circuit 980 for coordinated cardiac and neural stimulations. Examples of the cardiac stimulation circuit 980 include a pacing circuit, a cardioversion/defibrillation circuit, a CRT device, and/or an RCT device. Cardiac stimulation circuit 980 also provides for sensing of one or more cardiac signals including electrograms. In one embodiment, cardiac stimulation circuit 980 provides the one or more signals indicative of autonomic activities. In various embodiments, implantable medical device 910 further includes one or more of a drug delivery device, a biological therapy device, and any other device that supplements the functions of neural stimulation circuit 930 and cardiac stimulation circuit 980. Implant telemetry circuit 974 communicates with external system 120 via telemetry link 125.

In one embodiment, one or more sensors 990 are coupled to implantable medical devices 910 via one or more electrical connections and/or telemetry links. Sensor(s) 990 are external to implantable medical devices 910 and perform, for example, one or more functions of heart rate sensing circuit 862, activity sensing circuit 864, respiration sensing circuit 866, impedance sensing circuit 868, heart sound sensing circuit 870, and pressure sensing circuit 872. In general, various specific embodiments of system 100 use physiological sensors that are external to implantable medical device 110 and communicate with implantable medical device 110 via electrical connections and/or telemetry links. Such physiological sensors include implantable sensors, external sensors, or both.

Figure 10:
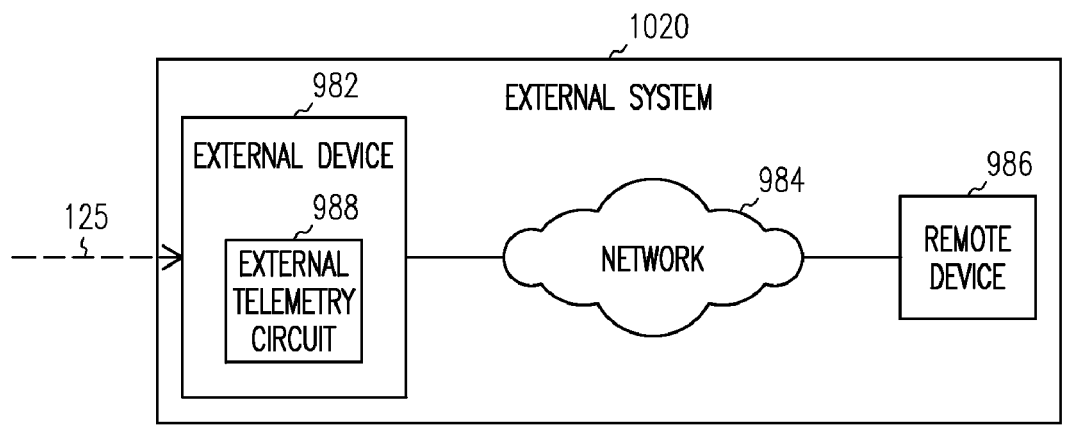
FIG. 10 is a block diagram illustrating an embodiment of an external system communicating with the implantable medical device.

FIG. 10 is a block diagram illustrating an embodiment of an external system 1020, which is a specific embodiment of external system 120. As illustrated in FIG. 10, external system 1020 is a patient management system including an external device 982, a telecommunication network 984, and a remote device 986. External device 982 is placed within the vicinity of implantable medical device 110 or 910 and includes external telemetry system 988 to communicate with the implantable medical device via telemetry link 125. Remote device 986 is in a remote location and communicates with external device 982 through network 984, thus allowing a physician or other caregiver to monitor and treat a patient from a distant location and/or allowing access to various treatment resources from the remote location.

According to the present subject matter, neural stimulation pulses are delivered to the sympathetic nervous system and the parasympathetic nervous system through one or more neural leads. In various embodiments, neural signals are sensed from the sympathetic nervous system and the parasympathetic nervous system through the one or more neural leads. Examples of sites to which the neural stimulation pulses are delivered and from which neural signals are sense include a site in a pulmonary artery in a proximity of a high concentration of baroreceptors, a cardiac fat pad, an aortic nerve, a carotid nerve, a vagus nerve, a vascular site proximal to the aortic, carotid, or vagus nerve, and sites in the spinal cord, on the spinal cord dorsal or ventral nerves, or in the sympathetic ganglia or nerves. Electrodes of the one or more neural leads are placed in one or more such sites for neural sensing and stimulation.

A brief discussion of the physiology related to baroreceptors and chemoreceptors is provided below. This brief discussion introduces the autonomic nervous system, baroreflex, and chemoreceptors to provide an understanding of placement of the electrodes (also referred to as neural traffic sensors) of the neural leads.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 11B:
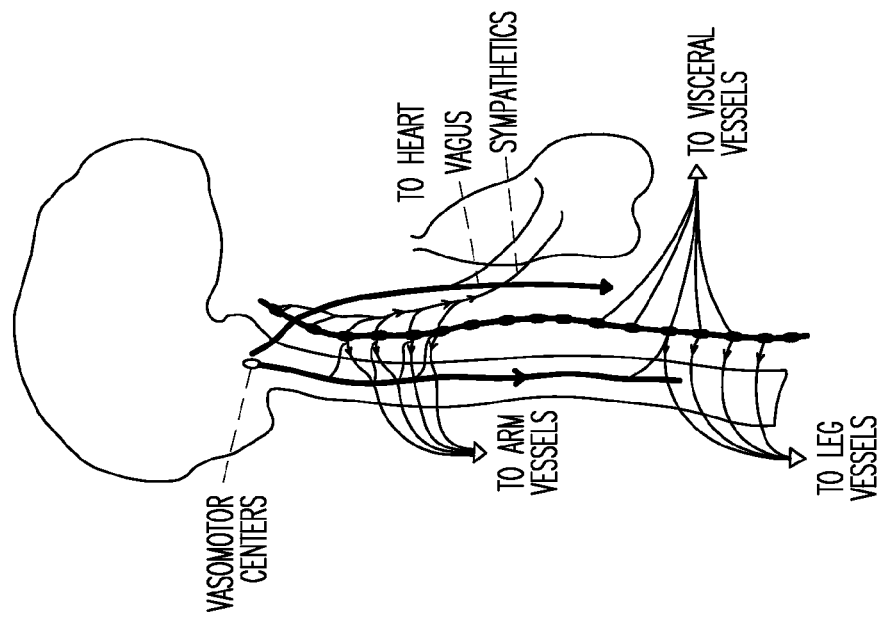
FIGS. 11A and 11B are illustrations of neural mechanisms for peripheral vascular control.
Figure 11A:
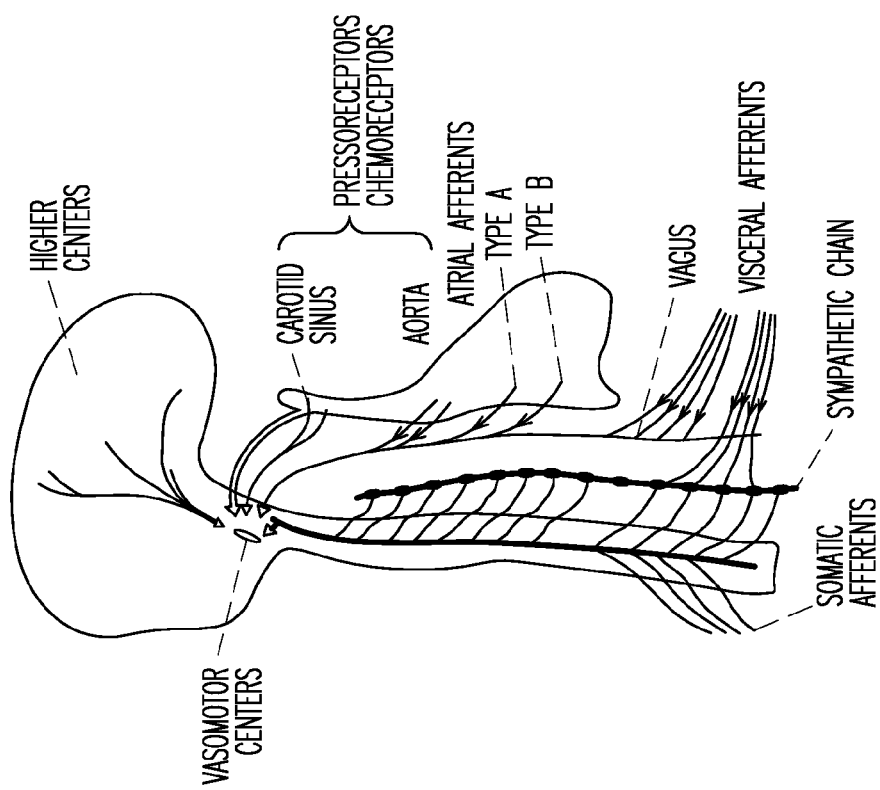

In various embodiments, neural stimulation is applied to affect the heart rate, blood pressure, vasodilation, and vasoconstriction. The heart rate and contractile strength is increased when excitatory stimulation is applied to the sympathetic nervous system and when inhibitory stimulation is applied the parasympathetic nervous system, and is decreased when inhibitory stimulation is applied the sympathetic nervous system or when excitatory stimulation is applied the parasympathetic nervous system. In various embodiments, nerve traffic is also sensed to provide a surrogate parameter for another physiological parameter, such as heart rate, blood pressure and the like. FIGS. 11A and 11B illustrate neural mechanisms for peripheral vascular control. FIG. 11A generally illustrates afferent nerves to vasomotor centers. An afferent nerve conveys impulses toward a nerve center. A vasomotor center relates to nerves that dilate and constrict blood vessels to control the size of the blood vessels. FIG. 11B generally illustrates efferent nerves from vasomotor centers. An efferent nerve conveys impulses away from a nerve center.

Stimulation of the sympathetic and parasympathetic nervous systems is known to have effects other than heart rate, contractile strength, and blood pressure. For example, excitatory stimulation of the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Excitatory stimulation of the parasympathetic nervous system and/or inhibitory stimulation of the sympathetic nervous system constrict the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems. Additionally, sensing of nerve traffic for use as a surrogate parameter of a physiological parameter can depend on a number of physiological parameters. Various embodiments of the present subject matter perturb the physiological system with precisely located neural stimulation, and monitor the nerve traffic response to the stimulation.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that provide baroreceptor fields that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Thus, physiological parameters, such as systemic arterial pressure, can be determined based on nerve traffic. Such pressure information, for example, provides useful feedback information to guide therapy such as neural therapy or cardiac stimulation therapy such as CRT.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerves can also be electrically stimulated to induce a baroreflex, which inhibits the sympathetic nerve activity and stimulates parasympathetic nerve activity. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall).

Some aspects of the present subject matter locally sense specific nerve endings in vessel walls rather than or in addition to afferent and/or efferent nerve trunks. For example, some embodiments sense baroreceptor sites or fields in the pulmonary artery. Some embodiments of the present subject matter involve sensing baroreceptor sites or nerve endings in the aorta, the chambers of the heart, some embodiments of the present subject matter involve sensing efferent pathways such as the fat pads of the heart, and some embodiments of the present subject matter involve stimulating an afferent nerve trunk, such as the vagus, carotid and aortic nerves. Various embodiments involve combinations of sensing nerve ending, sensing efferent nerve pathways and sensing afferent nerve pathways. Some embodiments sense nerve trunks using a cuff electrode, and some embodiments sense nerve trunks using an intravascular lead positioned in a blood vessel proximate to the nerve. Examples of afferent nerve trunks include the vagus, aortic and carotid nerves. Examples of efferent nerve trunks include the cardiac branches of the vagus nerve. Stimulation of efferent nerves such as these cardiac branches or the nerves in cardiac fat pads conveys nervous impulses to an effector, and thus do not use the baroreflex negative feedback of the central nervous system, which responds to nerve activity on afferent nerves with nerve activity on efferent nerves. Some embodiments sense neural traffic at any of the above-identified neural stimulation sites.

Figure 12B:
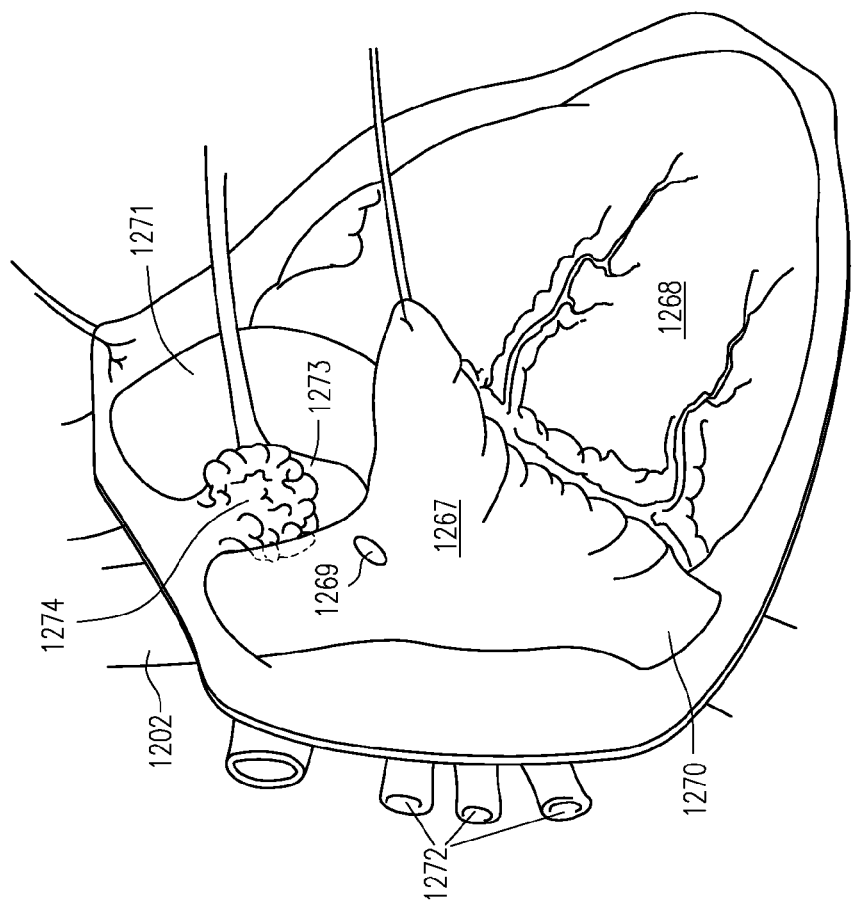
FIGS. 12A-C are illustrations of a heart.
Figure 12A:
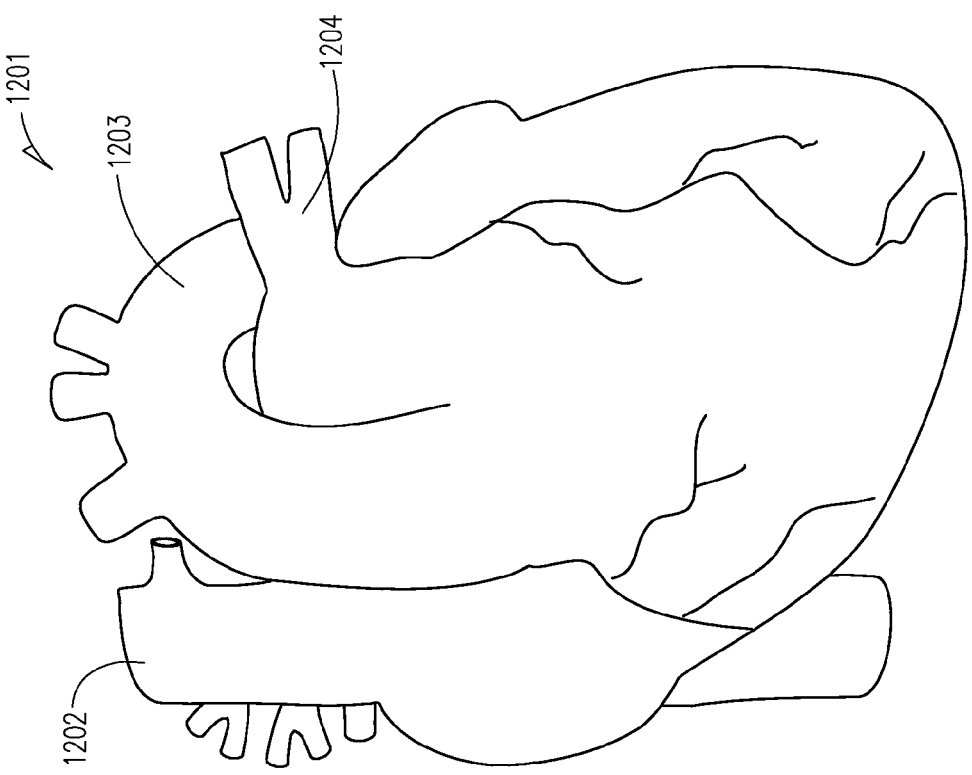
Figure 12C:
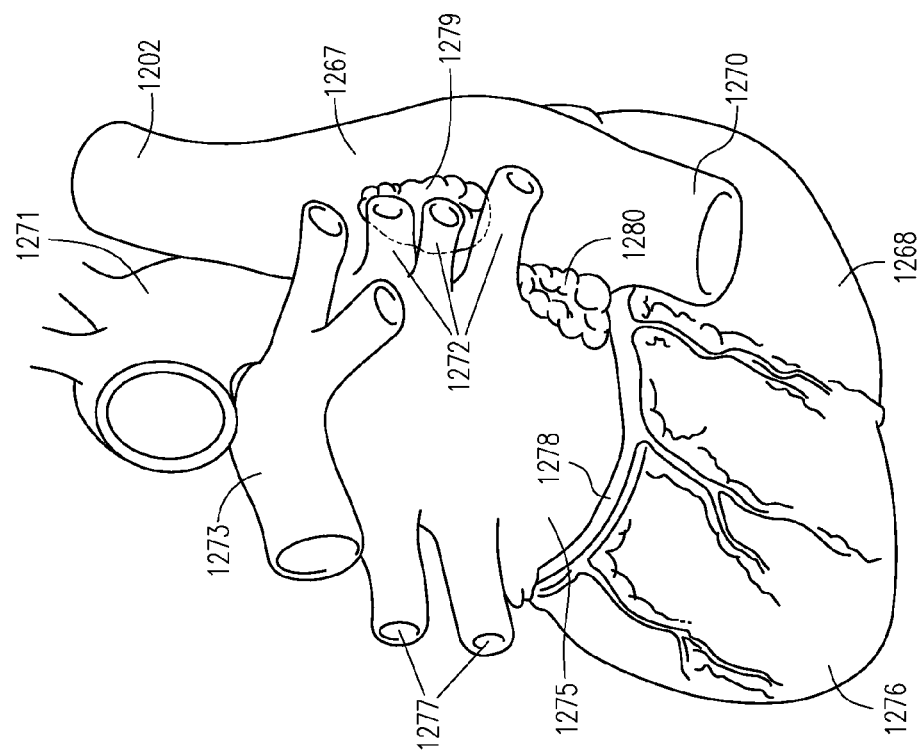

FIGS. 12A-12C illustrate a heart. As illustrated in FIG. 12A, the heart 1201 includes a superior vena cava 1202, an aortic arch 1203, and a pulmonary artery 1204. As is discussed in more detail below, pulmonary artery 1204 includes baroreceptors. A lead is capable of being intravascularly inserted through a peripheral vein and through the tricuspid valve into the right ventricle of the heart (not expressly shown in the figure) similar to a cardiac pacing lead, and continue from the right ventricle through the pulmonary valve into the pulmonary artery. A portion of the pulmonary artery and aorta are proximate to each other. Various embodiments sense neural activity by the baroreceptor in the aorta using a lead intravascularly positioned in the pulmonary artery. Some embodiments also stimulate baroreceptors in the aorta. Aspects of the present subject matter provide a relatively noninvasive surgical technique to implant a neural traffic sensor, with or without a baroreceptor stimulator, intravascularly into the pulmonary artery.

FIGS. 12B-12C illustrate the right side and left side of the heart, respectively, and further illustrate cardiac fat pads. FIG. 12B illustrates the right atrium 1267, right ventricle 1268, sinoatrial node 1269, superior vena cava 1202, inferior vena cava 1270, aorta 1271, right pulmonary veins 1272, and right pulmonary artery 1273. FIG. 12B also illustrates a cardiac fat pad 1274 between superior vena cava 1202 and aorta 1271. Autonomic ganglia in cardiac fat pad 1274 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 12C illustrates the left atrium 1275, left ventricle 1276, right atrium 1267, right ventricle 1268, superior vena cava 1202, inferior vena cava 1270, aorta 1271, right pulmonary veins 1272, left pulmonary vein 1277, right pulmonary artery 1273, and coronary sinus 1278. FIG. 12C also illustrates a cardiac fat pad 1279 located proximate to the right cardiac veins and a cardiac fat pad 1280 located proximate to inferior vena cava 1270 and left atrium 1275. Autonomic ganglia in cardiac fat pad 1279 are stimulated and/or nerve traffic is sensed in some embodiments using an electrode screwed or otherwise inserted into cardiac fat pad 1279, and are stimulated and/or nerve traffic is sensed in some embodiments using an intravenously-fed lead proximately positioned to the fat pad in a vessel such as right pulmonary artery 1273 or right pulmonary vein 1272, for example. Autonomic ganglia in cardiac fat pad 1280 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as inferior vena cava 1270 or coronary sinus 1278 or a lead in left atrium 1275, for example.

Figure 13:
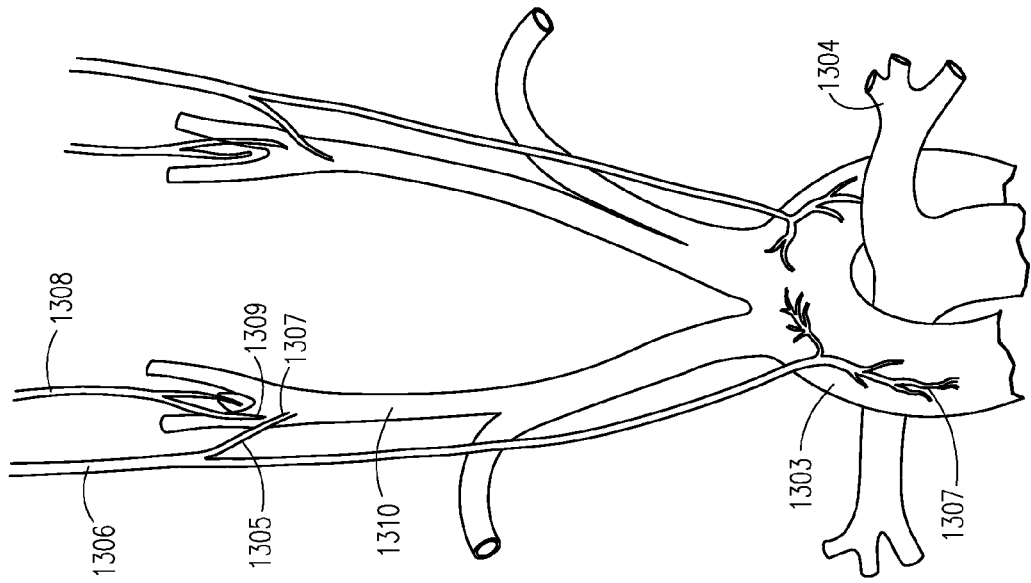
FIG. 13 is an illustration of baroreceptors and afferent nerves in the area of the carotid sinuses and aortic arch.

FIG. 13 illustrates baroreceptors in the area of the carotid sinus 1305, aortic arch 1303 and pulmonary artery 1304. The aortic arch 1303 and pulmonary artery 1304 were previously illustrated with respect to the heart in FIG. 12A. As illustrated in FIG. 13, the vagus nerve 1306 extends and provides sensory nerve endings 1307 that function as baroreceptors in the aortic arch 1303, in carotid sinus 1305 and in the common carotid artery 1310. The glossopharyngeal nerve 1308 provides nerve endings 1309 that function as baroreceptors in carotid sinus 1305. These nerve endings 1307 and 1309, for example, are sensitive to stretching of the wall resulting from increased pressure from within. Activation of these nerve endings reduces pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. In various embodiments, afferent nerve trunks are stimulated, and/or nerve traffic from the afferent nerve trunks are sensed, using a cuff or intravascularly-fed lead positioned in a blood vessel proximate to the afferent nerves.

Figure 14:
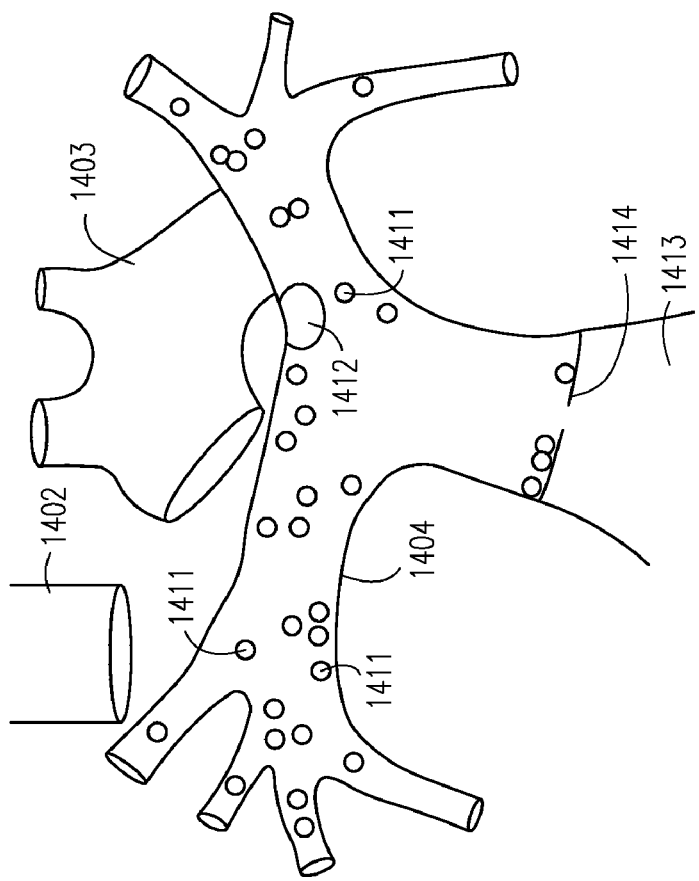
FIG. 14 is an illustration of baroreceptors in and around the pulmonary artery.

FIG. 14 illustrates baroreceptors in and around a pulmonary artery 1404. The superior vena cava 1402 and the aortic arch 1403 are also illustrated. As illustrated, pulmonary artery 1404 includes a number of baroreceptors 1411. Furthermore, a cluster of closely spaced baroreceptors is situated near the attachment of the ligamentum arteriosum 1412. FIG. 14 also illustrates the right ventricle 1413 of the heart, and the pulmonary valve 1414 separating right ventricle 1413 from pulmonary artery 1404. According to various embodiments of the present subject matter, a lead is inserted through a peripheral vein and threaded through the tricuspid valve into the right ventricle, and from right ventricle 1413 through pulmonary valve 1414 and into pulmonary artery 1404 to stimulate baroreceptors and/or sense nerve traffic from the baroreceptors in and/or around the pulmonary artery. In various embodiments, for example, the lead is positioned to stimulate the cluster of baroreceptors and/or sense nerve traffic near ligamentum arteriosum 1412.

Figure 15:
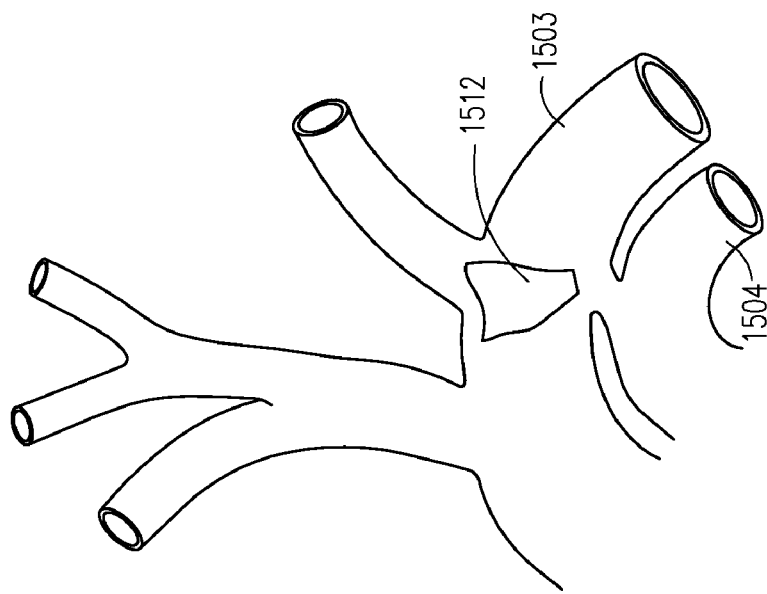
FIG. 15 is an illustration of baroreceptor fields in the aortic arch, the ligamentum arteriosum and the trunk of the pulmonary artery.

FIG. 15 illustrates baroreceptor fields 1512 in the aortic arch 1503, near the ligamentum arteriosum and the trunk of the pulmonary artery 1504. Some embodiments position the lead in the pulmonary artery to stimulate baroreceptor sites and/or sense nerve traffic in the aorta and/or cardiac fat pads, such as are illustrated in FIGS. 12B-12C.

Figure 16:
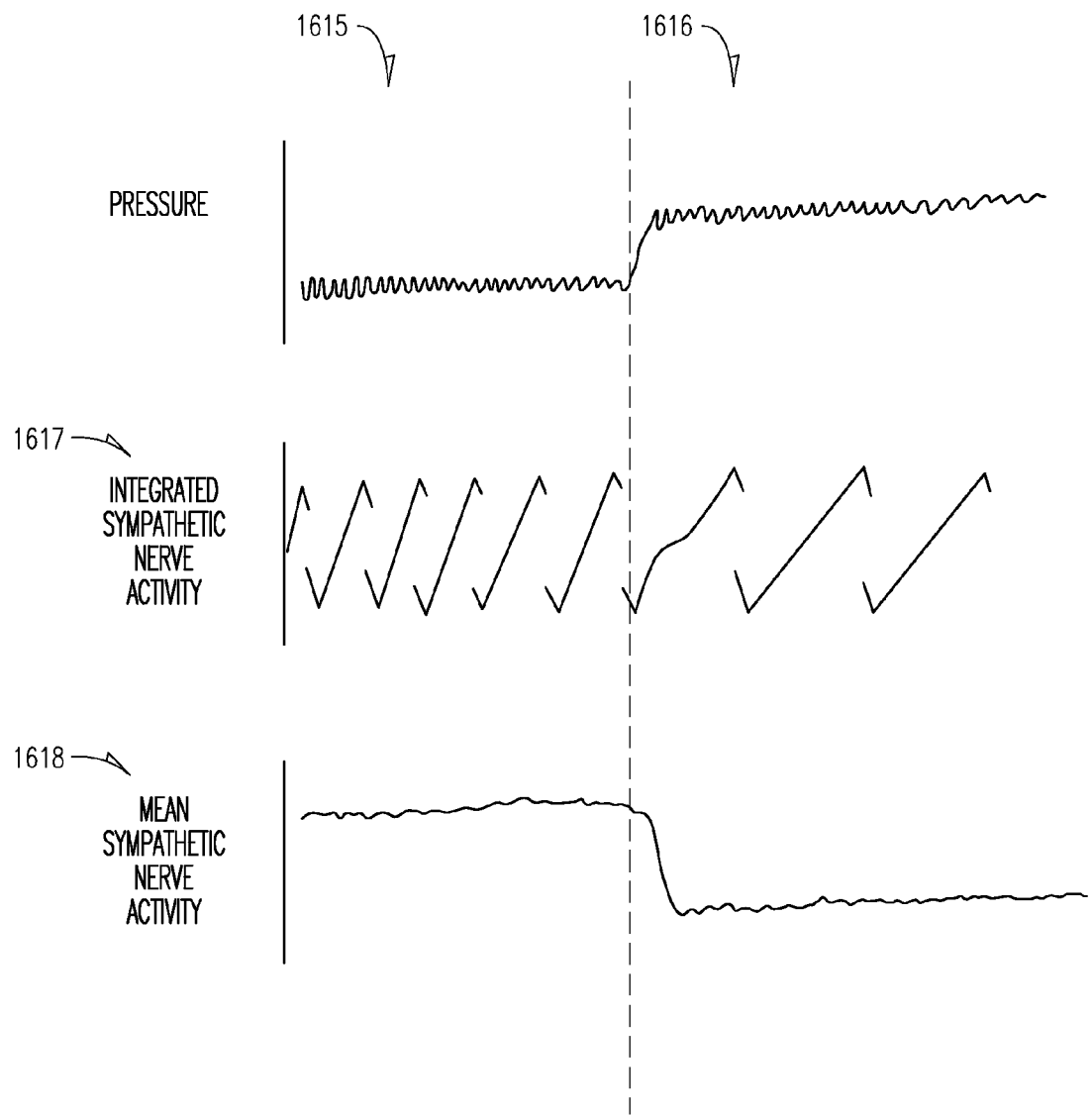
FIG. 16 is an illustration of an example of a neural response after perturbing a physiological system.

FIG. 16 illustrates an example of a neural response after perturbing a physiological system. In this example, pressure functions as an indicator for a physiological system. The pressure is experimentally induced, leading to a reflex inhibition of sympathetic activity. The system is illustrated in a first low pressure condition 1615 and a second high pressure condition 1616. Nerve activity, illustrated as waveforms 1617 and 1618, changes between the two conditions. The change may be rather transient in nature if the nervous system quickly adapts from the first to the second condition, or may be more sustained if the nervous system does not quickly adapt to the change in conditions. Regardless, an analysis of a sensed nerve traffic signal can extract or otherwise determine features of the signal indicative of the response. In the illustrated example, waveform 1617 associated with an integrated sympathetic nerve activity changes (e.g. change in slope and period of waveform) from the first to the second conditions. Additionally, waveform 1618 associated with a mean sympathetic nerve activity changes (e.g. a first level of nerve activity to a second level of nerve activity) from the first to the second conditions. The integrated sympathetic nerve activity and mean sympathetic nerve activity waveforms are provided as examples. Other ways of sensing changes in the neural traffic signals can be used.

Various embodiments of the present subject matter sense nerve traffic corresponding to chemoreceptors. The carotid and aortic bodies provide a concentration of cardiovascular chemoreceptors. The carotid body lies deep to the bifurcation of the common carotid artery or somewhat between the two branches. The carotid body is a small, flattened, oval structure, 2 to 5 mm in diameter, with a characteristic structure composed of epithelioid cells, which are in close relation to capillary sinusoids, and an abundance of nerve fibers. Surrounding the carotid body is a delicate fibrous capsule. It is part of the visceral afferent system of the body, containing chemoreceptor endings that respond to low levels of oxygen in the blood or high levels of carbon dioxide and lowered pH of the blood. It is supplied by nerve fibers from both the glossopharyngeal and vagus nerves.

The aortic bodies (glomera aortica) are chemoreceptors similar to the carotid bodies. Afferent fibers from the aortic bodies run in the right vagus and have cell bodies in the inferior ganglion. The supracardial bodies (aortic paraganglia) are also chemoreceptors with their afferent fibers in the left vagus and cell bodies in the inferior ganglion.

In various embodiments of the present subject matter, neural signals are sensed, and neural therapies are delivered, by an implantable system including an implantable medical device such as an implantable neural stimulation device or an integrated cardiac and neural stimulation device. Although implantable systems are illustrated and discussed, various aspects and embodiments of the present subject matter can be implemented in external devices. For example, neural signals can be sensed, and neural stimulation can be delivered, using implantable leads, external electrodes, percutaneous leads, or any combination of these.

Figure 17:
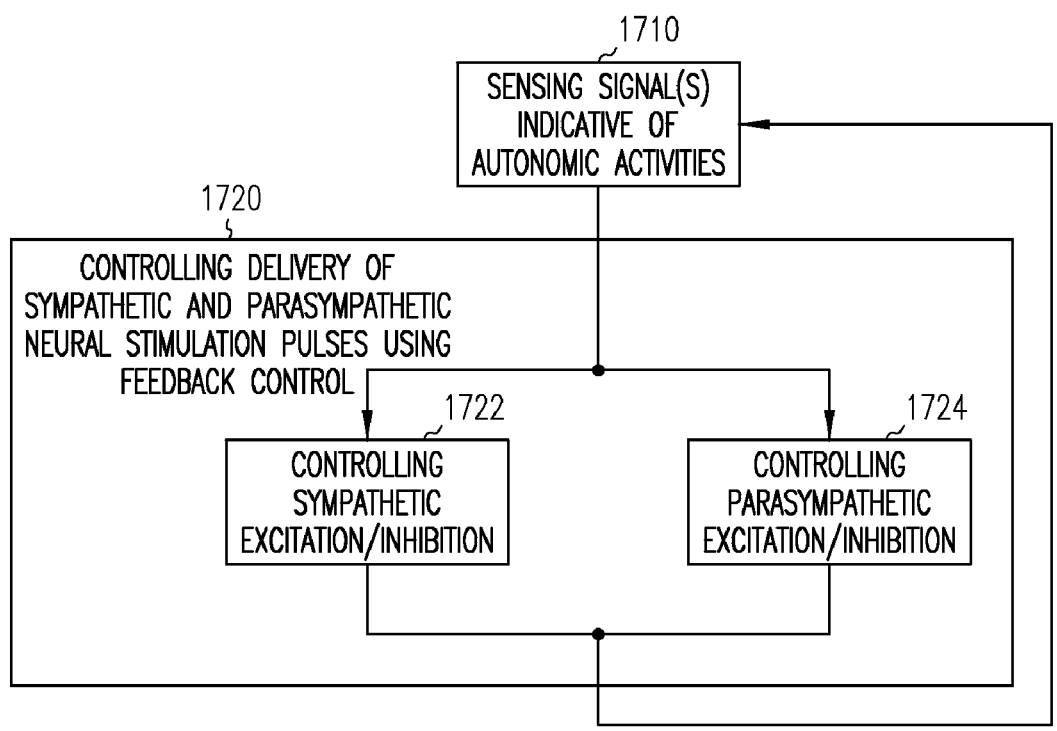
FIG. 17 is a flow chart illustrating an embodiment of a method of neural stimulation for controlling autonomic balance.

FIG. 17 is a flow chart illustrating an embodiment of a method of neural stimulation for controlling autonomic balance. In one embodiment, the method is performed by system 100.

One or more signals indicative of autonomic activities are sensed at 1710. Examples of such signals include neural signals, surrogate signals, and physiological function signals. The neural signals directly indicate the autonomic state. In one embodiment, the neural signals include at least one sympathetic neural signal indicative of sympathetic nerve traffic and at least one parasympathetic neural signal indicative of parasympathetic nerve traffic. The surrogate signals are each a signal known to indicate autonomic activities. In one embodiment, the LF/HF ratio is used as a surrogate signal being a surrogate of the autonomic state. The physiological function signals each indicate a physiological function controlled or affected by the autonomic activities. In one embodiment, the physiological function signals include one or more of signals indicative of heart rate, activity level, respiratory activities, transthoracic impedance, heart sounds, and blood pressures.

Delivery of sympathetic and parasympathetic stimulation pulses are controlled using feedback control at 1720. The one or more signals sensed at 1710 serve as input for the feedback control. As illustrated in FIG. 17, the feedback control is applied to control the delivery of the sympathetic stimulation pulses for sympathetic excitation and sympathetic inhibition at 1722 and to control the delivery of the parasympathetic stimulation pulses for parasympathetic excitation and parasympathetic inhibition at 1724. In one embodiment, the delivery of sympathetic and parasympathetic stimulation pulses is controlled to achieve a desired autonomic balance. In one embodiment, the delivery of sympathetic and parasympathetic stimulation pulses is controlled to shift autonomic balance for a predetermined period of time. The autonomic balance is shifted in one direction by increasing sympathetic tone and/or decreasing parasympathetic tone or in the other direction by decreasing sympathetic tone and/or increasing parasympathetic tone. In one embodiment, the delivery of sympathetic and parasympathetic stimulation pulses is controlled to control the autonomic balance according to a predetermined schedule. For example, the autonomic balance is shifted to result in a desirable performance of a physiological function when the use of that function is anticipated for certain times of day.

The delivery of the sympathetic and parasympathetic stimulation pulses are controlled by adjusting a plurality of stimulation parameters based on the one or more signals indicative of autonomic activities. This includes adjusting one or more sympathetic stimulation parameters controlling the sympathetic excitation and the sympathetic inhibition and one or more parasympathetic stimulation parameters controlling the parasympathetic excitation and the parasympathetic inhibition. In one embodiment, the stimulation parameters are adjusted based on one or more neural signals sensed at 1710. In another embodiment, the stimulation parameters are adjusted based on one or more surrogate signals sensed at 1710. In another embodiment, the stimulation parameters are adjusted based on one or more physiological function signals sensed at 1710. In another embodiment, the stimulation parameters are adjusted based on the one or more neural signals and the one or more physiological function signals. In another embodiment, the stimulation parameters are adjusted based on the one or more surrogate signals and the one or more physiological function signals.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of legal equivalents to which such claims are entitled.

What is claimed is:

1. A neural stimulation system for stimulating at least a sympathetic nerve and a parasympathetic nerve, the system comprising:
   a stimulation output circuit configured to deliver sympathetic stimulation pulses to the sympathetic nerve and parasympathetic stimulation pulses to the parasympathetic nerve; and
   a stimulation control circuit coupled to the stimulation output circuit and the autonomic balance monitoring circuit, the stimulation control circuit configured to control the delivery of the sympathetic stimulation pulses and the parasympathetic stimulation pulses to increase sympathetic tone and decrease parasympathetic tone or to decrease sympathetic tone and increase parasympathetic tone.

2. The system of claim 1, further comprising an autonomic balance monitoring circuit configured to sense one or more signals indicative of autonomic activities, and wherein the stimulation control circuit comprises a stimulation parameter adjustment circuit configured to adjust a plurality of stimulation parameters controlling the delivery of the sympathetic stimulation pulses and the parasympathetic stimulation pulses using the one or more signals indicative of autonomic activities.

3. The system of claim 2, wherein the stimulation parameter adjustment circuit is configured to adjust the plurality of stimulation parameters using a predetermined time schedule.

4. The system of claim 2, wherein the autonomic balance monitoring circuit comprises a nerve traffic sensing circuit configured to sense one or more neural signals indicative of the autonomic activities including nerve traffic, and the stimulation parameter adjustment circuit is configured to adjust the plurality of stimulation parameters using the one or more neural signals.

5. The system of claim 4, wherein the nerve traffic sensing circuit comprises:
   a sympathetic traffic sensing circuit configured to sense at least one sympathetic neural signal indicative of sympathetic nerve traffic; and
   a parasympathetic traffic sensing circuit configured to sense at least one parasympathetic neural signal indicative of parasympathetic nerve traffic.

6. The system of claim 2, wherein the autonomic balance monitoring circuit comprises a heart rate variability (HRV) sensing circuit configured to sense an HRV and produce a surrogate signal using the sensed HRV, and the stimulation parameter adjustment circuit is configured to adjust the plurality of stimulation parameters using the surrogate signal.

7. The system of claim 2, wherein the autonomic balance monitoring circuit comprises a physiological function sensing circuit configured to sense one or more physiological function signals each indicative of one of more physiological functions related to the autonomic activities, and the stimulation parameter adjustment circuit is configured to adjust the plurality of stimulation parameters using the one or more physiological function signals.

8. The system of claim 7, wherein the physiological function sensing circuit comprises a heart rate sensing circuit configured to sense a signal indicative of heart rate.

9. The system of claim 7, wherein the physiological function sensing circuit comprises an activity sensing circuit configured to sense a signal indicative of physical activity level.

10. The system of claim 7, wherein the physiological function sensing circuit comprises a respiration sensing circuit configured to sense a respiratory signal.

11. The system of claim 7, wherein the physiological function sensing circuit comprises an impedance sensing circuit configured to sense a signal indicative of a transthoracic impedance or a cardiac impedance.

12. The system of claim 7, wherein the physiological function sensing circuit comprises a heart sound sensing circuit configured to sense a signal indicative of heart sounds.

13. The system of claim 7, wherein the physiological function sensing circuit comprises a pressure sensing circuit configured to sense a signal indicative of a blood pressure.

14. The system of claim 2, further comprising an implantable medical device including the stimulation output circuit, the autonomic balance monitoring circuit, and the stimulation control circuit.

15. A neural stimulation system for stimulating at least a sympathetic nerve and a parasympathetic nerve, the system comprising:
   a stimulation output circuit configured to deliver sympathetic stimulation pulses to the sympathetic nerve and parasympathetic stimulation pulses to the parasympathetic nerve;
   an autonomic balance monitoring circuit configured to sense one or more signals indicative of autonomic activities; and
   a stimulation control circuit coupled to the stimulation output circuit and the autonomic balance monitoring circuit, the stimulation control circuit configured to control the delivery of the sympathetic stimulation pulses and the parasympathetic stimulation pulses to increase sympathetic tone and decrease parasympathetic tone using the one or more signals indicative of autonomic activities.

16. The system of claim 15, comprising an implantable medical device including the stimulation output circuit, the autonomic balance monitoring circuit, and the stimulation control circuit.

17. The system of claim 16, wherein the implantable medical device further comprises a cardiac stimulation circuit configured to deliver cardiac stimulation pulses in coordination with the delivery of the sympathetic stimulation pulses and parasympathetic stimulation pulses.

18. A neural stimulation system for stimulating at least a sympathetic nerve and a parasympathetic nerve, the system comprising:
   a stimulation output circuit configured to deliver sympathetic stimulation pulses to the sympathetic nerve and parasympathetic stimulation pulses to the parasympathetic nerve;
   an autonomic balance monitoring circuit configured to sense one or more signals indicative of autonomic activities; and
   a stimulation control circuit coupled to the stimulation output circuit and the autonomic balance monitoring circuit, the stimulation control circuit configured to control the delivery of the sympathetic stimulation pulses and the parasympathetic stimulation pulses to decrease sympathetic tone and increase parasympathetic tone using the one or more signals indicative of autonomic activities.

19. The system of claim 18, comprising an implantable medical device including the stimulation output circuit, the autonomic balance monitoring circuit, and the stimulation control circuit.

20. The system of claim 19, wherein the implantable medical device further comprises a cardiac stimulation circuit configured to deliver cardiac stimulation pulses in coordination with the delivery of the sympathetic stimulation pulses and parasympathetic stimulation pulses.

* * * * *